United States Patent
Lippert et al.

(10) Patent No.: US 9,957,284 B2
(45) Date of Patent: May 1, 2018

(54) METHOD OF INCREASING MASS TRANSFER RATE OF ACID GAS SCRUBBING SOLVENTS

(71) Applicant: University of Kentucky Research Foundation, Lexington, KY (US)

(72) Inventors: Cameron A. Lippert, Lexington, KY (US); Kunlei Liu, Lexington, KY (US); Christine Marie Brandewie, Lexington, KY (US); Joseph Eugene Remias, Woodbridge, VA (US); Moushumi Sarma, Lexington, KY (US)

(73) Assignee: UNIVERSITY OF KENTUCKY RESEARCH FOUNDATION, Lexington, KY (US)

( * ) Notice: Subject to any disclaimer, the term of this patent is extended or adjusted under 35 U.S.C. 154(b) by 61 days.

(21) Appl. No.: 14/593,399

(22) Filed: Jan. 9, 2015

(65) Prior Publication Data
US 2015/0196875 A1   Jul. 16, 2015

Related U.S. Application Data

(60) Provisional application No. 61/925,693, filed on Jan. 10, 2014.

(51) Int. Cl.
| | | |
|---|---|---|
| *B01D 53/14* | (2006.01) | |
| *C07F 1/08* | (2006.01) | |
| *C07F 1/10* | (2006.01) | |
| *C07F 1/12* | (2006.01) | |
| *C07F 3/06* | (2006.01) | |
| *C07F 3/08* | (2006.01) | |
| *C07F 3/10* | (2006.01) | |
| *C07F 9/00* | (2006.01) | |
| *C07F 11/00* | (2006.01) | |
| *C07F 13/00* | (2006.01) | |

(Continued)

(52) U.S. Cl.
CPC ............ *C07F 3/06* (2013.01); *B01D 53/1475* (2013.01); *C07F 19/00* (2013.01); *B01D 2252/20421* (2013.01); *B01D 2252/20426* (2013.01); *B01D 2252/20431* (2013.01); *B01D 2252/602* (2013.01); *B01D 2255/20792* (2013.01); *Y02C 10/06* (2013.01); *Y02P 20/152* (2015.11)

(58) Field of Classification Search
None
See application file for complete search history.

(56) References Cited

U.S. PATENT DOCUMENTS

| | | |
|---|---|---|
| 4,231,995 A | 11/1980 | Campbell et al. |
| 5,674,459 A | 10/1997 | Gohara et al. |
| 6,890,497 B2 | 5/2005 | Rau et al. |

(Continued)

FOREIGN PATENT DOCUMENTS

WO   1999026714 A1   6/1999

OTHER PUBLICATIONS

Zeng et al., "Synthesis, Oxygenation and Catalytic Oxidation Performance of Crown Ether-Containing Schiff Base-Transition Metal Complexes." Adv. Synth. Catal. (2004), 346, 1385-1391.*

*Primary Examiner* — Daniel Berns
(74) *Attorney, Agent, or Firm* — King & Schickli, PLLC

(57) ABSTRACT

A method and catalysts for increasing the overall mass transfer rate of acid gas scrubbing solids is disclosed. Various catalyst compounds for that purpose are also disclosed.

8 Claims, 2 Drawing Sheets

(51) Int. Cl.
*C07F 15/00* (2006.01)
*C07F 19/00* (2006.01)

(56) References Cited

U.S. PATENT DOCUMENTS

| | | | |
|---|---|---|---|
| 6,923,852 B2 | 8/2005 | Vrotsos |
| 7,255,842 B1 | 8/2007 | Yeh et al. |
| 7,282,189 B2 | 10/2007 | Zauderer |
| 7,514,053 B2 | 4/2009 | Johnson et al. |
| 7,618,478 B2 | 11/2009 | Kumar |
| 7,678,351 B2 | 3/2010 | Iyer et al. |
| 7,699,909 B2 | 4/2010 | Lackner et al. |
| 7,722,842 B2 | 5/2010 | Park et al. |
| 7,739,864 B2 | 6/2010 | Finkenrath et al. |
| 7,766,999 B2 | 8/2010 | Ha |
| 7,794,690 B2 | 9/2010 | Abatzoglou et al. |
| 7,811,359 B2 | 10/2010 | Tandon et al. |
| 7,819,951 B2 | 10/2010 | White et al. |
| 7,827,778 B2 | 11/2010 | Finkenrath et al. |
| 7,829,053 B2 | 11/2010 | Constantz |
| 7,833,328 B2 | 11/2010 | Lackner et al. |
| 7,842,126 B1 | 11/2010 | Dilmore et al. |
| 7,842,264 B2 | 11/2010 | Cooper et al. |
| 7,846,240 B2 | 12/2010 | Gal et al. |
| 7,846,407 B2 | 12/2010 | Hu |
| 7,850,763 B2 | 12/2010 | White et al. |
| 7,862,788 B2 | 1/2011 | Gal et al. |
| 7,879,305 B2 | 2/2011 | Reddy et al. |
| 7,887,694 B2 | 2/2011 | Constantz et al. |
| 7,895,822 B2 | 3/2011 | Hoffmann et al. |
| 7,896,694 B2 | 3/2011 | Schumann et al. |
| 7,896,953 B1 | 3/2011 | Goswami et al. |
| 7,901,485 B2 | 3/2011 | McCutchen |
| 7,901,487 B2 | 3/2011 | Rochelle |
| 7,901,488 B2 | 3/2011 | Rochelle et al. |
| 7,906,086 B2 | 3/2011 | Comrie |
| 7,914,758 B2 | 3/2011 | Murray et al. |
| 7,922,792 B1 | 4/2011 | Soong et al. |
| 7,947,239 B2 | 5/2011 | Lackner et al. |
| 7,947,240 B2 | 5/2011 | Vandor |
| 7,966,829 B2 | 6/2011 | Finkenrath et al. |
| 7,993,432 B2 | 8/2011 | Wright et al. |
| 8,012,453 B2 | 9/2011 | Saxena |

* cited by examiner

METHOD OF INCREASING MASS TRANSFER RATE OF ACID GAS SCRUBBING SOLVENTS

This document claims priority of U.S. Provisional Patent Application Ser. No. 61/925,693, filed on Jan. 10, 2014, the full disclosure of which is incorporated herein by reference.

TECHNICAL FIELD

The present invention relates generally to various methods and catalysts for increasing the overall mass transfer rate of acid gas scrubbing solvents utilizing various catalyst compounds.

BACKGROUND

The cleanup of acid gasses or sour gas, such as $CO_2$ in particular, from natural gas and in oil refining has been an extensively practiced technology. The industrial removal of $CO_2$ from natural gas dates back to the 1930's. In the $21^{st}$ century, due to the potential impact of anthropogenic $CO_2$ emissions on the climate, post-combustion $CO_2$ capture has gained tremendous attention. While several technologies exist for the removal of acid gasses one of the most commonly employed practices is the use of aqueous amines. Of these amines, tertiary amines are often used for natural gas applications due to their low energy of regeneration. For post-combustion $CO_2$ capture applications primary and secondary amines tend to be in part favored by their faster rate at the low gaseous $CO_2$ concentration condition. Regardless of the application, the mass transfer rate in the absorber column dictates the size of the column (capital cost) used and, consequently, has a substantial impact on the overall process cost. A simplified process depicting a thermal swing process is presented in FIG. 1. An aqueous amine solution is circulated between the absorber 10 and stripper 12. The gas, containing $CO_2$, enters the bottom of the absorber where it contacts the aqueous amine absorbent removing it from the gas stream. The liquid solution, $CO_2$ rich amine solution, is then passed through a heat exchanger 14 to improve efficiency before being heated to a higher temperature in the stripper 12. The stripper 12 removes the $CO_2$ as a gas from the amine solution to produce a lean, or $CO_2$ deficient solution. The lean solution is returned to the absorber 10 by way of the heat exchanger 14 to repeat the process.

In order to minimize system capital (absorber cost) it is important to maximize the overall mass transfer rate for the scrubber system as there is a direct correlation between the two. This invention relates to methods for this purpose as well as to catalyst compounds useful in those methods.

SUMMARY

A method is provided for increasing the overall mass transfer rate of acid gas scrubbing solvents. The method comprises adding a catalyst compound to a fluid stream including an acid gas and an acid gas scrubbing solvent wherein that catalyst compound has a chemical formula:

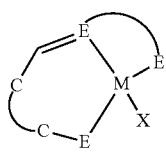

where:
(a) M is any group VII B through XII B element;
(b) x=neutral sigma donor or monovalent anion;
(c)

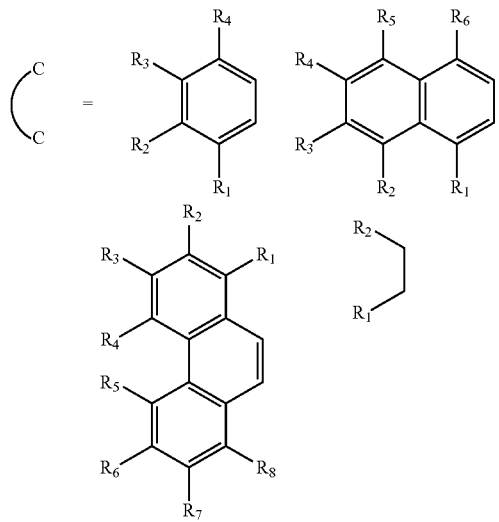

where $R_1$=H, any alkyl, RCOOH (R=alkyl ranging from 0-10 carbons); OligoPEG, phosphate, ROH (R=alkyl ranging from 0-5 carbons), —[$OCH_2CH_2$]-m (m=number of repeat units); OH; $SO_3$; $NO_2$; amine, amide, carbonyl, Cl, Br, I, F, $BH_3$, $[CH_2Q]^+[A]^-$ $R_2$=H, any alkyl, RCOOH (R=alkyl ranging from 0-10 carbons); OligoPEG, phosphate, ROH (R=alkyl ranging from 0-5 carbons), —[$OCH_2CH_2$]-m (m=number of repeat units); OH; $SO_3$; $NO_2$; amine, amide, carbonyl Cl, Br, I, F, $BH_3$, $[CH_2Q]^+[A]^-$ $R_3$=H, any alkyl, RCOOH (R=alkyl ranging from 0-10 carbons); OligoPEG, phosphate, ROH (R=alkyl ranging from 0-5 carbons), —[$OCH_2CH_2$]-m (m=number of repeat units); OH; $SO_3$; $NO_2$; amine, amide, carbonyl Cl, Br, I, F, $BH_3$, $[CH_2Q]^+[A]^-$ $R_4$=H, any alkyl, RCOOH (R=alkyl ranging from 0-10 carbons); OligoPEG, phosphate, ROH (R=alkyl ranging from 0-5 carbons), —[$OCH_2CH_2$]-m (m=number of repeat units); OH; $SO_3$; $NO_2$; amine, amide, carbonyl Cl, Br, I, F, $BH_3$, $[CH_2Q]^+[A]^-$ $R_5$=H, any alkyl, RCOOH (R=alkyl ranging from 0-10 carbons); OligoPEG, phosphate, ROH (R=alkyl ranging from 0-5 carbons), —[$OCH_2CH_2$]-m (m=number of repeat units); OH; $SO_3$; $NO_2$; amine, amide, carbonyl Cl, Br, I, F, $BH_3$, $[CH_2Q]^+[A]^-$ $R_6$=H, any alkyl, RCOOH (R=alkyl ranging from 0-10 carbons); OligoPEG, phosphate, ROH (R=alkyl ranging from 0-5 carbons), —[$OCH_2CH_2$]-m (m=number of repeat units); OH; $SO_3$; $NO_2$; amine, amide, carbonyl Cl, Br, I, F, $BH_3$, $[CH_2Q]^+[A]^-$ $R_7$=H, any alkyl, RCOOH (R=alkyl ranging from 0-10 carbons); OligoPEG, phosphate, ROH (R=alkyl ranging from 0-5 carbons), —[$OCH_2CH_2$]-m (m=number of repeat units); OH; $SO_3$; $NO_2$; amine, amide, carbonyl Cl, Br, I, F, $BH_3$, $[CH_2Q]^+[A]^-$ $R_8$=H, any alkyl, RCOOH (R=alkyl ranging from 0-10 carbons); OligoPEG, phosphate, ROH (R=alkyl ranging from 0-5 carbons), —[$OCH_2CH_2$]-m (m=number of repeat units); OH; SO$_3$; NO$_2$; amine, amide, carbonyl Cl, Br, I, F, BH$_3$, [CH$_2$Q]$^+$[A]$^-$; and

[CH$_2$Q]$^+$[A]$^-$=

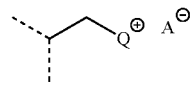

where A=monovalent anion: Cl, Br, I, F, PF$_6$, BF$_4$, acetate, trifluoroacetate, ClO$_4$, NO$_3$, and Q=monovalent cation: PR$_3$, R=alkyl, cyclic alkyl, Aryl, O-alkyl, O-Aryl NR$_3$, R=alkyl, cyclic alkyl, N-heterocyclic ring, imidazole; and (d)

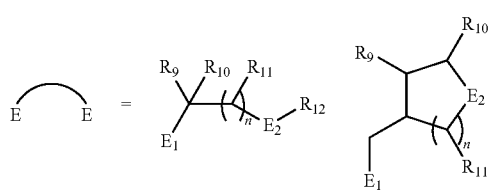

where E$_1$=N, P, S, B

E$_2$=N, P, S, O, B n=1-10.

In an alternative embodiment, the method comprises adding a catalyst compound to a fluid stream including an acid gas and an acid gas scrubbing solvent wherein that catalyst compound has a chemical formula:

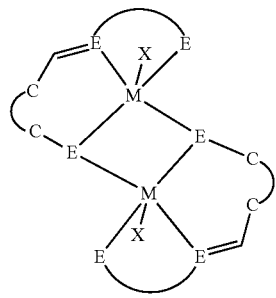

where:

M is any group VII B through XII B element;

(b) x=neutral sigma donor or monovalent anion;

(c)

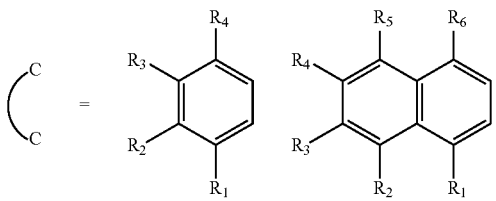

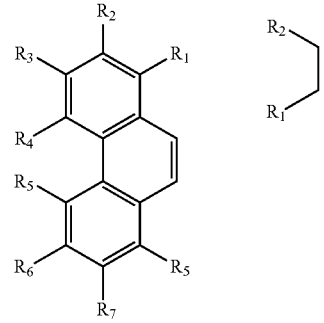

where R$_1$=H, any alkyl, RCOOH (R=alkyl ranging from 0-10 carbons); OligoPEG, phosphate, ROH (R=alkyl ranging from 0-5 carbons), —[OCH$_2$CH$_2$]-m (m=number of repeat units); OH; SO$_3$; NO$_2$; amine, amide, carbonyl, Cl, Br, I, F, BH$_3$, [CH$_2$Q]$^+$[A]$^-$ R$_2$=H, any alkyl, RCOOH (R=alkyl ranging from 0-10 carbons); OligoPEG, phosphate, ROH (R=alkyl ranging from 0-5 carbons), —[OCH$_2$CH$_2$]-m (m=number of repeat units); OH; SO$_3$; NO$_2$; amine, amide, carbonyl Cl, Br, I, F, BH$_3$, [CH$_2$Q]$^+$[A]$^-$ R$_3$=H, any alkyl, RCOOH (R=alkyl ranging from 0-10 carbons); OligoPEG, phosphate, ROH (R=alkyl ranging from 0-5 carbons), —[OCH$_2$CH$_2$]-m (m=number of repeat units); OH; SO$_3$; NO$_2$; amine, amide, carbonyl Cl, Br, I, F, BH$_3$, [CH$_2$Q]$^+$[A]$^-$ R$_4$=H, any alkyl, RCOOH (R=alkyl ranging from 0-10 carbons); OligoPEG, phosphate, ROH (R=alkyl ranging from 0-5 carbons), —[OCH$_2$CH$_2$]-m (m=number of repeat units); OH; SO$_3$; NO$_2$; amine, amide, carbonyl Cl, Br, I, F, BH$_3$, [CH$_2$Q]$^+$[A]$^-$ R$_5$=H, any alkyl, RCOOH (R=alkyl ranging from 0-10 carbons); OligoPEG, phosphate, ROH (R=alkyl ranging from 0-5 carbons), —[OCH$_2$CH$_2$]-m (m=number of repeat units); OH; SO$_3$; NO$_2$; amine, amide, carbonyl Cl, Br, I, F, BH$_3$, [CH$_2$Q]$^+$[A]$^-$ R$_6$=H, any alkyl, RCOOH (R=alkyl ranging from 0-10 carbons); OligoPEG, phosphate, ROH (R=alkyl ranging from 0-5 carbons), —[OCH$_2$CH$_2$]-m (m=number of repeat units); OH; SO$_3$; NO$_2$; amine, amide, carbonyl Cl, Br, I, F, BH$_3$, [CH$_2$Q]$^+$[A]$^-$ R$_7$=H, any alkyl, RCOOH (R=alkyl ranging from 0-10 carbons); OligoPEG, phosphate, ROH (R=alkyl ranging from 0-5 carbons), —[OCH$_2$CH$_2$]-m (m=number of repeat units); OH; SO$_3$; NO$_2$; amine, amide, carbonyl Cl, Br, I, F, BH$_3$, [CH$_2$Q]$^+$[A]$^-$ R$_8$=H, any alkyl, RCOOH (R=alkyl ranging from 0-10 carbons); OligoPEG, phosphate, ROH (R=alkyl ranging from 0-5 carbons), —[OCH$_2$CH$_2$]-m (m=number of repeat units); OH; SO$_3$; NO$_2$; amine, amide, carbonyl Cl, Br, I, F, BH$_3$, [CH$_2$Q]$^+$[A]$^-$; and

[CH$_2$Q]$^+$[A]$^-$=

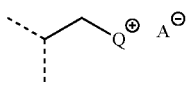

where A=monovalent anion: Cl, Br, I, F, PF$_6$, BF$_4$, acetate, trifluoroacetate, ClO$_4$, NO$_3$, and Q=monovalent cation: PR$_3$, R=alkyl, cyclic alkyl, Aryl, O-alkyl, O-Aryl $NR_3$, R=alkyl, cyclic alkyl, N-heterocyclic ring, imidazole (d)

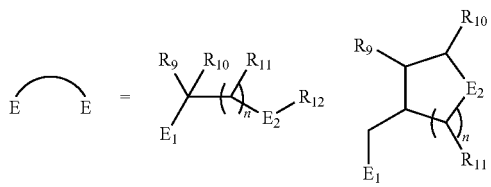

where $E_1$=N, P, S, B $E_2$=N, P, S, O, B n=1-10.

In yet another embodiment, the method comprises adding a catalyst compound to a fluid stream including an acid gas and an acid gas scrubbing solvent wherein that catalyst compound has a chemical formula:

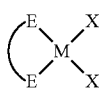

where:

(a) M is any group VII B through XII B element;

(b) x=neutral sigma donor or monovalent anion; and (c)

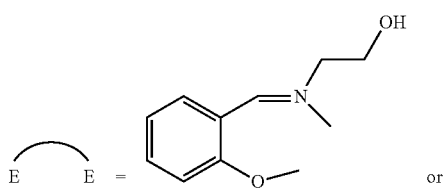

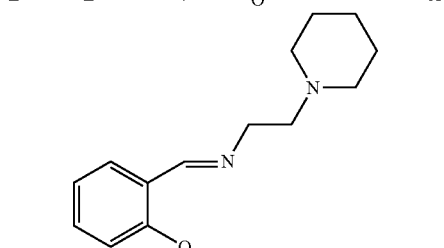

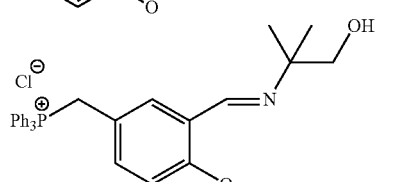

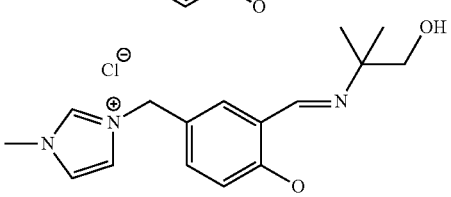

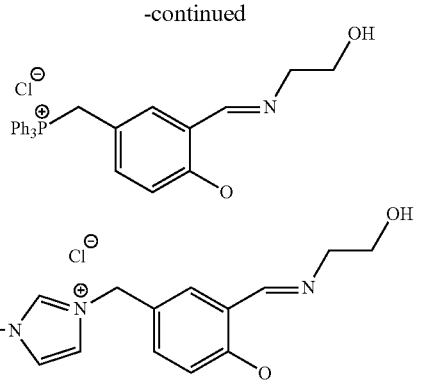

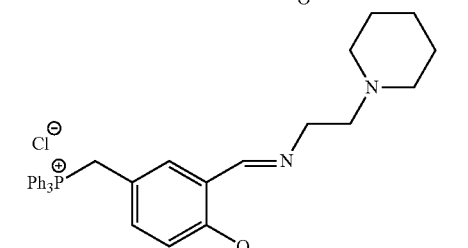

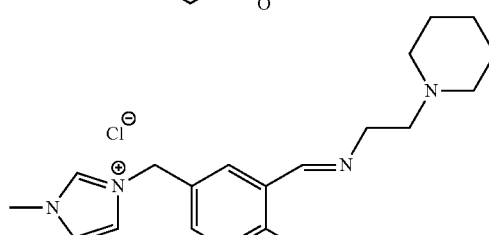

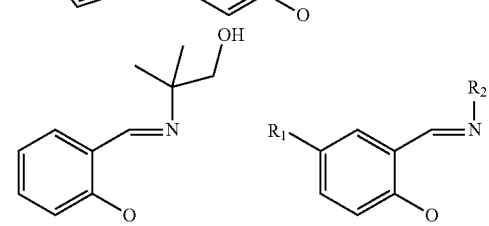

$R_1$=H, any alkyl, RCOOH (R=alkyl ranging from 0-10 carbons); OligoPEG, phosphate, ROH (R=alkyl ranging from 0-5 carbons), —[$OCH_2CH_2$] and repeats thereof; OH; $SO_3$; $NO_2$; amine, amide, carbonyl, Cl, Br, I, F, $BH_3$, [$CH_2Q$]+[A]−; and

[$CH_2Q$]+[A]−=

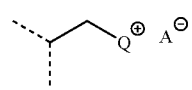

where A=monovalent anion: Cl, Br, I, F, $PF_6$, $BF_4$, acetate, trifluoroacetate, $ClO_4$, $NO_3$, and Q=monovalent cation: P(R)$_3$, R=alkyl, cyclic alkyl, Aryl, O-alkyl, O-Aryl;

$NR_3$, R=alkyl, cyclic alkyl, N-heterocyclic ring, imidazole; and $R_2$=CE; where C=any alkyl, cyclic alkyl, aryl, and E=OH, $NH_2$, N(R)$_3$, R=alkyl, cyclic alkyl, N-heterocyclic ring, imidazole, morpholine.

In one possible embodiment, the catalysts compound has a chemical formula:

In one possible embodiment, the catalysts compound has a chemical formula:

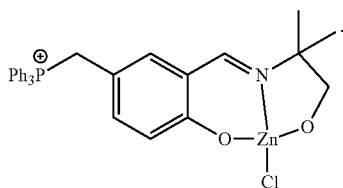

In one possible embodiment, the catalysts compound has a chemical formula:

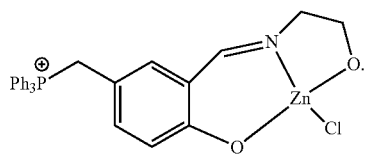

In one possible embodiment, the catalysts compound has a chemical formula:

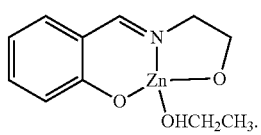

In one possible embodiment, the catalysts compound has a chemical formula:

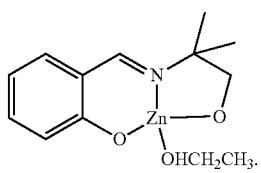

In one possible embodiment, the catalysts compound has a chemical formula:

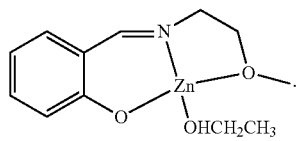

In one possible embodiment, the catalysts compound has a chemical formula:

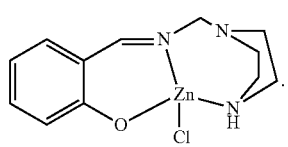

In one possible embodiment, the catalysts compound has a chemical formula:

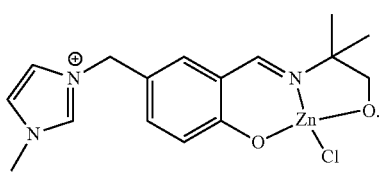

In one possible embodiment, the catalysts compound has a chemical formula:

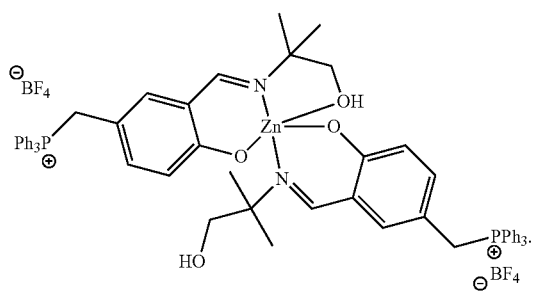

In one possible embodiment, the catalysts compound has a chemical formula:

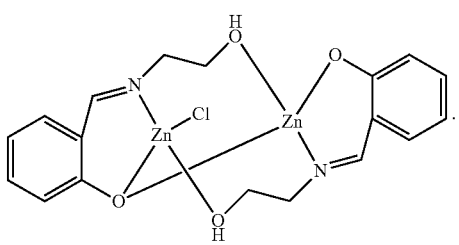

In one possible embodiment, the catalysts compound has a chemical formula:

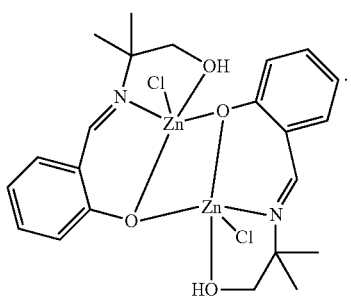

In any of the embodiments, the neutral sigma donor or monovalent anion may be selected from a group consisting of $H_2O$, Cl, Br, F, I, acetate, triflate, perchlorate, nitro, pyridine, ethanol, methanol, tetrahydrofuran, dimethylsulfoxide, carbonate, bicarbonate, sulfate, nitrate and nitrite.

In any of the embodiments, the acid gas scrubbing solvent includes an amine or a mixture of amines, and/or no-amine based solvent such as alkali carbonate/bicarbonate solution. In one possible embodiment the acid gas scrubbing solvent includes a mixture of (a) a promoter amine and (b) a tertiary amine.

In one possible embodiment, the acid gas scrubbing solvent includes chemical compounds selected from a group including but not limited to, monoethanolamine (MEA), 1-amino-2-propanol (1A2P), 3-amino-1-propanol, 2-amino-1-propanol, 2-amino-1-butanol, 1-amino-2-butanol, 3-amino-2-butanol, 2-(methylamino)ethanonol (MAE), 2-(ethylamino)ethanol, morpholine, piperazine (PZ), 1-methylpiperazine (NMP), 2-methylpiperazine, hydroxypiperadine, 2-piperidineethanol, N-aminoethylpierazine (AEP), aminopropylmorpholine, 4-aminopiperidine, 2-amino-2-methyl-1-propanol (AMP), diethanolamine (DEA), diisopropanolamine (DIPA), glycine, alanine, β-alannine, sarcosine, ethylene diamine (EDA), 1,3-propanediamine, 1,4-butanediamine, 1,5-pentanediamine, 1,6-hexanediamine, methyldiethanolamine (MDEA), triethanolamine (TEA), dimethylethanolamine (DMEA), N,N,N',N'-tetramethyl-1,8-naphthalenediamine, diethylmonoethanolamine, dipropylmonoethanolamine, 1,4-dimethylpiperazine, N N,N',N'-tetramethyl-1,6-hexanediamine, N,N,N',N'-tetrakis (2-hydroxyethyl)ethylenediamine, N,N,N',N',N''-pentamethyldiethylenetriamine, N,N,N',N'-tetramethylethylenediamine, N,N,N',N'-tetramethylpropane-1,3-diamine, N,N,N', N'-tetramethylbutane-1,4-diamine, N,N,N',N'-tetramethyl-1,5-pentanediamine, alkali carbonate, and mixtures thereof.

Further the catalyst compound is provided at a concentration of between about 0.05 mM and about 100 mM.

Various catalyst compounds are also claimed.

BRIEF DESCRIPTION OF THE DRAWING FIGURES

The accompanying drawings incorporated herein and forming a part of the specification, illustrate several aspects of the present method and together with the description serve to explain certain principles thereof. In the drawings.

DETAILED DESCRIPTION

Figure 1:
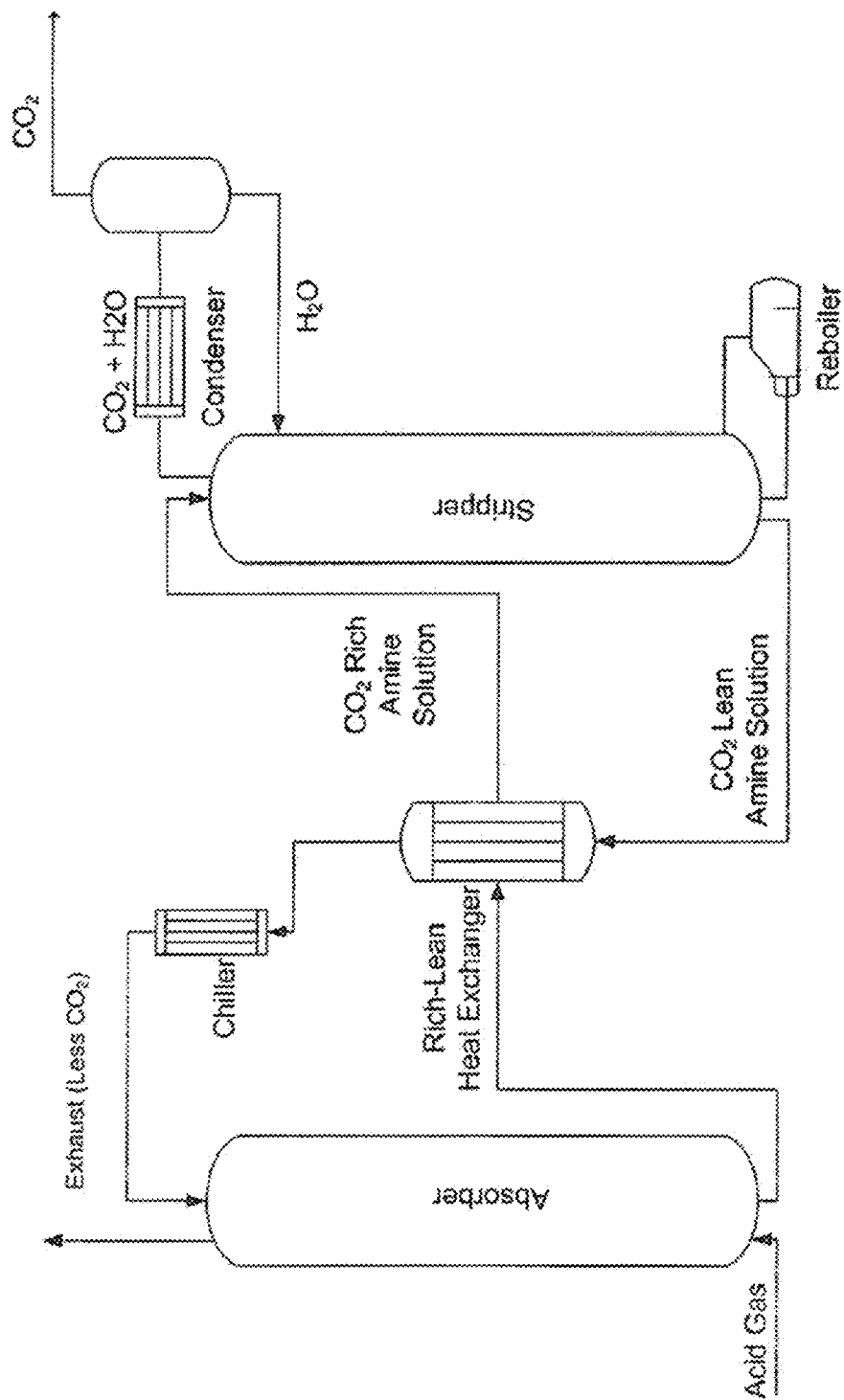
FIG. 1 is a schematical illustration of a process for removing acid gas from a fluid stream utilizing solvent and thermal swing regeneration.

This document relates generally to methods and catalysts for increasing overall mass transfer rate of acid gas scrubbing solvents as well as to novel transition metal monomer complexes incorporating a single transition metal atom.

The method may be broadly described as comprising adding a catalyst compound to a fluid stream including an acid gas and an acid gas scrubbing solvent. The catalyst compound has a chemical formula:

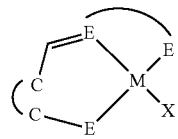

where:
(b) M is any group VII B through XII B element;
(b) x=neutral sigma donor or monovalent anion;
(c)

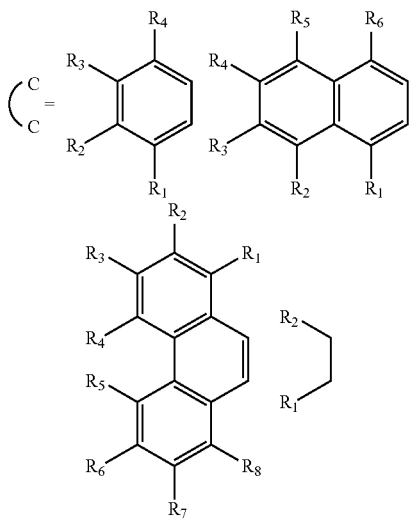

where R=H, any alkyl, RCOOH (R=alkyl ranging from 0-10 carbons); OligoPEG, phosphate, ROH (R=alkyl ranging from 0-5 carbons), —[OCH$_2$CH$_2$]-m (m=number of repeat units); OH; SO$_3$; NO$_2$; amine, amide, carbonyl, Cl, Br, I, F, BH$_3$, [CH$_2$Q]$^+$[A]$^-$ R$_2$=H, any alkyl, RCOOH (R=alkyl ranging from 0-10 carbons); OligoPEG, phosphate, ROH (R=alkyl ranging from 0-5 carbons), —[OCH$_2$CH$_2$]-m (m=number of repeat units); OH; SO$_3$; NO$_2$; amine, amide, carbonyl Cl, Br, I, F, BH$_3$, [CH$_2$Q]$^+$[A]$^-$ R$_3$=H, any alkyl, RCOOH (R=alkyl ranging from 0-10 carbons); OligoPEG, phosphate, ROH (R=alkyl ranging from 0-5 carbons), —[OCH$_2$CH$_2$]-m (m=number of repeat units); OH; SO$_3$; NO$_2$; amine, amide, carbonyl Cl, Br, I, F, BH$_3$, [CH$_2$Q]$^+$[A]$^-$ R$_4$=H, any alkyl, RCOOH (R=alkyl ranging from 0-10 carbons); OligoPEG, phosphate, ROH (R=alkyl ranging from 0-5 carbons), —[OCH$_2$CH$_2$]-m (m=number of repeat units); OH; SO$_3$; NO$_2$; amine, amide, carbonyl Cl, Br, I, F, BH$_3$, [CH$_2$Q]$^+$[A]$^-$ R$_5$=H, any alkyl, RCOOH (R=alkyl ranging from 0-10 carbons); OligoPEG, phosphate, ROH (R=alkyl ranging from 0-5 carbons), —[OCH$_2$CH$_2$]-m (m=number of repeat units); OH; SO$_3$; NO$_2$; amine, amide, carbonyl Cl, Br, I, F, BH$_3$, [CH$_2$Q]$^+$[A]$^-$ R$_6$=H, any alkyl, RCOOH (R=alkyl ranging from 0-10 carbons); OligoPEG, phosphate, ROH (R=alkyl ranging from 0-5 carbons), —[OCH$_2$CH$_2$]-m (m=number of repeat units); OH; SO$_3$; NO$_2$; amine, amide, carbonyl Cl, Br, I, F, BH$_3$, [CH$_2$Q]$^+$[A]$^-$ R$_7$=H, any alkyl, RCOOH (R=alkyl ranging from 0-10 carbons); OligoPEG, phosphate, ROH (R=alkyl ranging from 0-5 carbons), —[OCH$_2$CH$_2$]-m (m=number of repeat units); OH; SO$_3$; NO$_2$; amine, amide, carbonyl Cl, Br, I, F, BH$_3$, [CH$_2$Q]$^+$[A]$^-$ R$_8$=H, any alkyl, RCOOH (R=alkyl ranging from 0-10 carbons); OligoPEG, phosphate, ROH (R=alkyl ranging from 0-5 carbons), —[OCH$_2$CH$_2$]-m (m=number of repeat units); OH; SO$_3$; NO$_2$; amine, amide, carbonyl Cl, Br, I, F, BH$_3$, [CH$_2$Q]$^+$[A]$^-$; and

[CH$_2$Q]$^+$[A]$^-$=

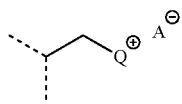

where A=monovalent anion: Cl, Br, I, F, PF$_6$, BF$_4$, acetate, trifluoroacetate, ClO$_4$, NO$_3$, and Q=monovalent cation: PR$_3$, R=alkyl, cyclic alkyl, Aryl, O-alkyl, O-Aryl NR$_3$, R=alkyl, cyclic alkyl, N-heterocyclic ring, imidazole; and (d)

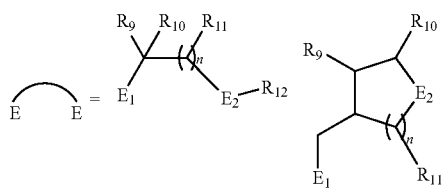

where E$_1$=N, P, S, B
E$_2$=N, P, S, O, B
n=1-10.

Specific catalyst compounds useful in this method include, but are not limited to the following:

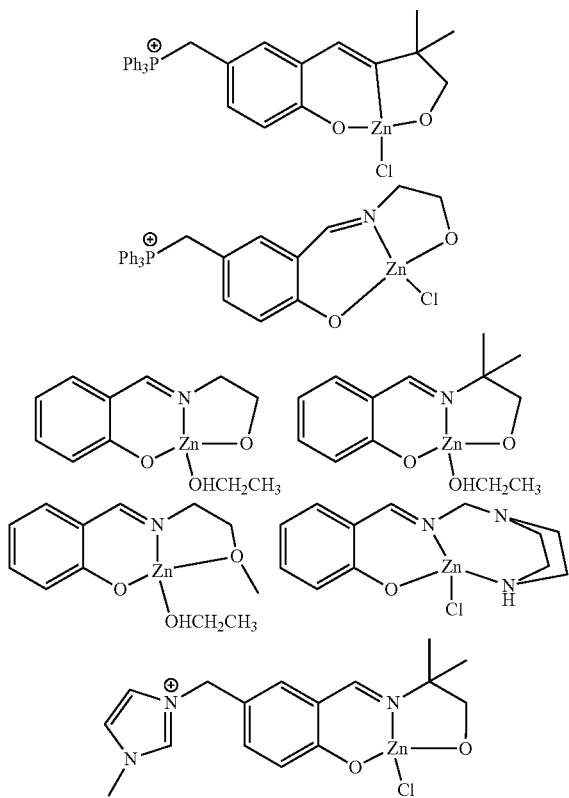

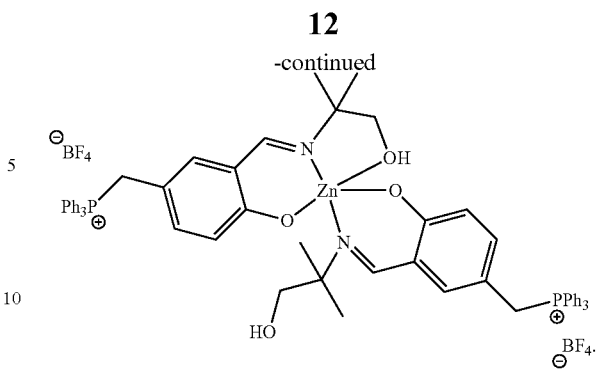

In another possible embodiment, the method may be broadly described as comprising adding a catalyst compound to a fluid stream including an acid gas and an acid gas scrubbing solvent. The catalyst compound has a chemical formula:

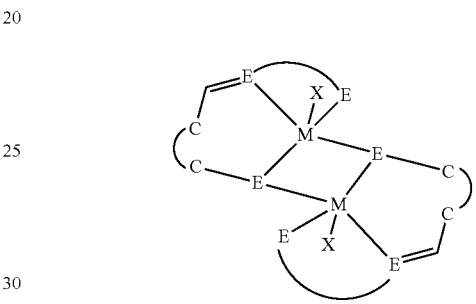

where:

(a) M is any group VII B through XII B element;
(b) x=neutral sigma donor or monovalent anion;
(c)

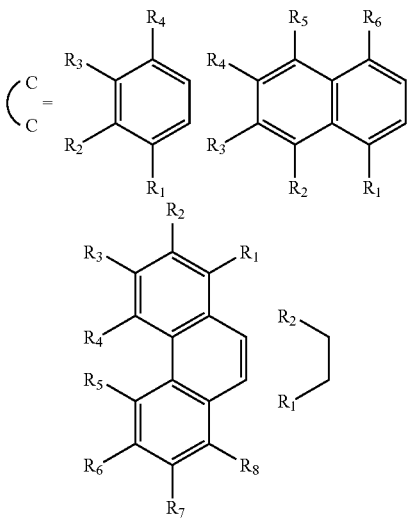

where R$_1$=H, any alkyl, RCOOH (R=alkyl ranging from 0-10 carbons); OligoPEG, phosphate, ROH (R=alkyl ranging from 0-5 carbons), —[OCH$_2$CH$_2$]-m (m=number of repeat units); OH; SO$_3$; NO$_2$; amine, amide, carbonyl, Cl, Br, I, F, BH$_3$, [CH$_2$Q]$^+$[A]$^-$ R$_2$=H, any alkyl, RCOOH (R=alkyl ranging from 0-10 carbons); OligoPEG, phosphate, ROH (R=alkyl ranging from 0-5 carbons), —[OCH$_2$CH$_2$]-m (m=number of repeat units); OH; SO$_3$; NO$_2$; amine, amide, carbonyl Cl, Br, I, F, BH$_3$, [CH$_2$Q]$^+$[A]$^-$ R$_3$=H, any alkyl, RCOOH (R=alkyl ranging from 0-10 carbons); OligoPEG, phosphate, ROH (R=alkyl ranging from 0-5 carbons), —[OCH$_2$CH$_2$]-m (m=number of repeat units); OH; SO$_3$; NO$_2$; amine, amide, carbonyl Cl, Br, I, F, BH$_3$, [CH$_2$Q]$^+$[A]$^-$ R$_4$=H, any alkyl, RCOOH (R=alkyl ranging from 0-10 carbons); OligoPEG, phosphate, ROH (R=alkyl ranging from 0-5 carbons), —[OCH$_2$CH$_2$]-m (m=number of repeat units); OH; SO$_3$; NO$_2$; amine, amide, carbonyl Cl, Br, I, F, BH$_3$, [CH$_2$Q]$^+$[A]$^-$ R$_5$=H, any alkyl, RCOOH (R=alkyl ranging from 0-10 carbons); OligoPEG, phosphate, ROH (R=alkyl ranging from 0-5 carbons), —[OCH$_2$CH$_2$]-m (m=number of repeat units); OH; SO$_3$; NO$_2$; amine, amide, carbonyl Cl, Br, I, F, BH$_3$, [CH$_2$Q]$^+$[A]$^-$ R$_6$=H, any alkyl, RCOOH (R=alkyl ranging from 0-10 carbons); OligoPEG, phosphate, ROH (R=alkyl ranging from 0-5 carbons), —[OCH$_2$CH$_2$]-m (m=number of repeat units); OH; SO$_3$; NO$_2$; amine, amide, carbonyl Cl, Br, I, F, BH$_3$, [CH$_2$Q]$^+$[A]$^-$ R$_7$=H, any alkyl, RCOOH (R=alkyl ranging from 0-10 carbons); OligoPEG, phosphate, ROH (R=alkyl ranging from 0-5 carbons), —[OCH$_2$CH$_2$]-m (m=number of repeat units); OH; SO$_3$; NO$_2$; amine, amide, carbonyl Cl, Br, I, F, BH$_3$, [CH$_2$Q]$^+$[A]$^-$ R$_8$=H, any alkyl, RCOOH (R=alkyl ranging from 0-10 carbons); OligoPEG, phosphate, ROH (R=alkyl ranging from 0-5 carbons), —[OCH$_2$CH$_2$]-m (m=number of repeat units); OH; SO$_3$; NO$_2$; amine, amide, carbonyl Cl, Br, I, F, BH$_3$, [CH$_2$Q]$^+$[A]$^-$; and

[CH$_2$Q]$^+$[A]$^-$=

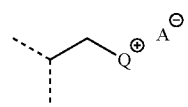

where A=monovalent anion: Cl, Br, I, F, PF$_6$, BF$_4$, acetate, trifluoroacetate, ClO$_4$, NO$_3$, and Q=monovalent cation: PR$_3$, R=alkyl, cyclic alkyl, Aryl, O-alkyl, O-Aryl NR$_3$, R=alkyl, cyclic alkyl, N-heterocyclic ring, imidazole (d)

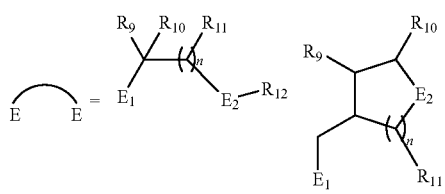

where E$_1$=N, P, S, B
E$_2$=N, P, S, O, B
n=1-10.

Specific catalyst compounds useful in this embodiment of the method include, but are not limited to the following:

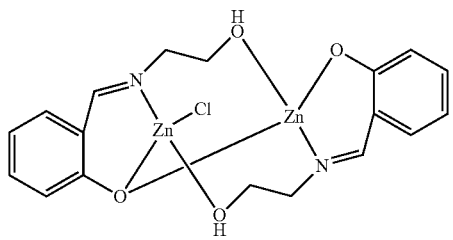

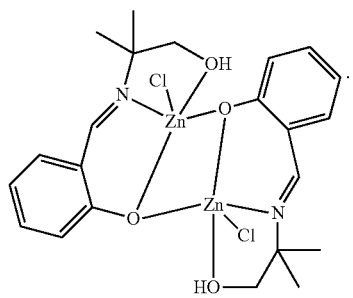

Still further, the method relates to a more efficient removal of carbon dioxide from a gaseous stream containing carbon dioxide and/or other acidic gases. In particular, the method separates carbon dioxide from a gas mixture using a combination of a homogeneous CO$_2$ hydration catalyst in the presence of an amine(s) and/or ionic carbonate/bicarbonate. The combination of catalyst and amine(s) and/or chemicals provides an overall increase in mass transfer rate resulting in either 1) lower capital cost for CCS due to smaller absorber tower, or 2) reduced energy cost in the stripper from obtaining a more carbon rich solution. The catalysts have the ability to react with CO$_2$ in the gas stream to form bicarbonate which reacts with the amine(s) to form an ammonium bicarbonate or carbamate where the CO$_2$ is now considered absorbed.

It was originally believed that CO$_2$ hydration catalyst required a 4-coordinate ligand in order to stabilize the metal center and show CO$_2$ hydration activity under carbon capture conditions. However, recent results obtained at the CAER show that catalysts containing 2-coordinate (bidentate) ligands of the general structure

are capable of increasing the overall mass transfer of carbon capture by aqueous capture solutions. A recent catalyst identified by the CAER

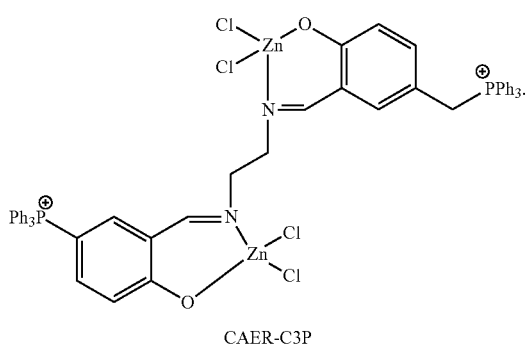

CAER-C3P

This catalyst contains a 2-coordinate, bidentate moiety from the ligand while monovalent anions occupy the other coordination sites.

Without limiting the scope of the method, a possible example of the system would consist of 0.001-0.1 wt % of catalyst containing a bidentate ligand and more than 20 wt % of amine(s), ethanolamine (MEA), methylydiethanolamine (MDEA), triethanolamine (TEA), dimethylethanolamine (DMEA), 1-amino-2-propanol (1A2P), 2-amino-1-propanol (1A2P), 3-aminopropanol, sodium ion, potassium ion, or combinations thereof, for examples.

Figure 2:
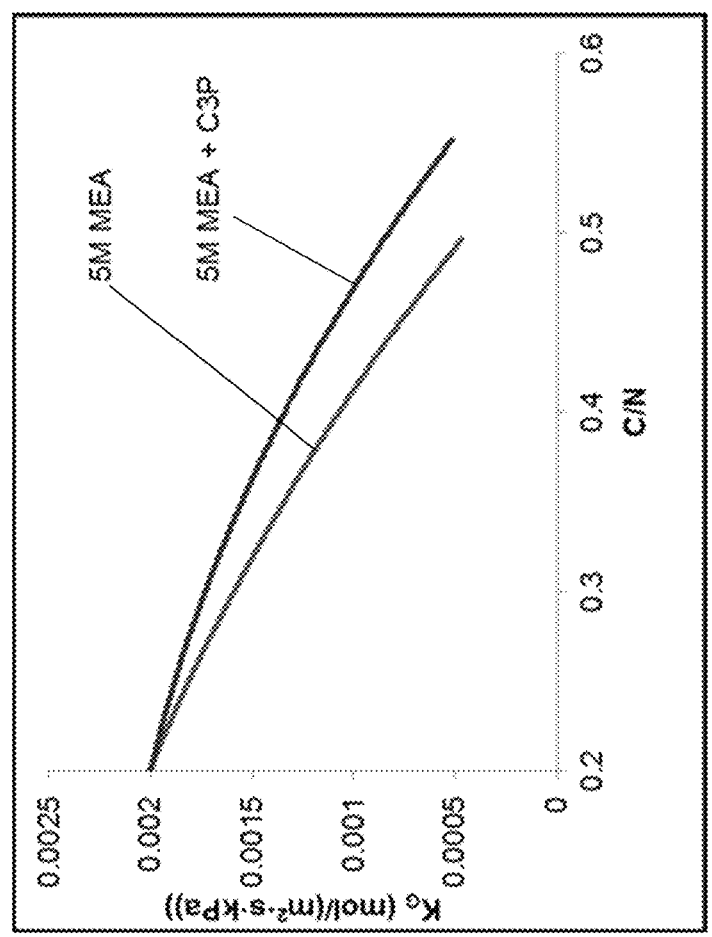
FIG. 2 is a plot of mass transfer coefficients versus carbon loading from WWC testing of 30 wt % MEA and 30 wt % MEA with 2 mM CAER-C3P at 40° C.

Addition of catalyst CAER-C3P (2 mM) to a 30% ethanolamine solution resulted in a ~25% increase in mass transfer rate over the working range of the solvent (see FIG. 2). As shown in FIG. 2, a greater enhancement in mass transfer is observed at higher carbon loadings (C/N>0.4, where C/N is the ratio of moles of carbon in solution compared to the moles of amine). This suggests that the rate of the catalyst is on the order of $10^5$ $M^{-1}s^{-1}$, two orders of magnitude higher than previous state-of-the-art catalyst, $[Zn(cyclen)(H_2O)]^{2+}$. Primary amines react very rapidly with $CO_2$ and in order for a catalyst to contribute to the overall mass transfer second order rate constants must of the magnitude of $10^5$ $M^{-1}s^{-1}$. This is the first example of catalysts containing a 2-coordinate, bidentate ligand showing activity in concentrated primary amine solutions.

The success of catalyst CAER-C3P in increasing overall mass transfer rates in 30 wt % MEA opened a new and novel area for catalyst development towards carbon capture purposes. Based on these results we developed a new family of $CO_2$ hydration catalysts that are less synthetically demanding than previous catalysts and thus more cost effective. That new catalyst family is schematically illustrated below.

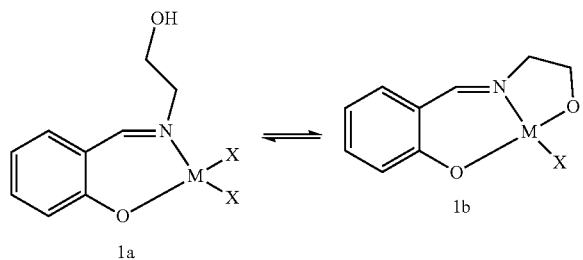

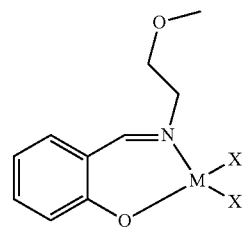

2

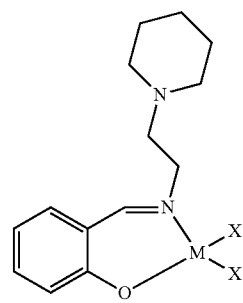

3

In another possible embodiment, the method may be broadly described as comprising adding a catalyst compound to a fluid stream including an acid gas and an acid gas scrubbing solvent. The catalyst compound has a chemical formula:

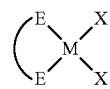

where:
(a) M is any group VII B through XII B element;
(b) x=neutral sigma donor or monovalent anion; and
(c)

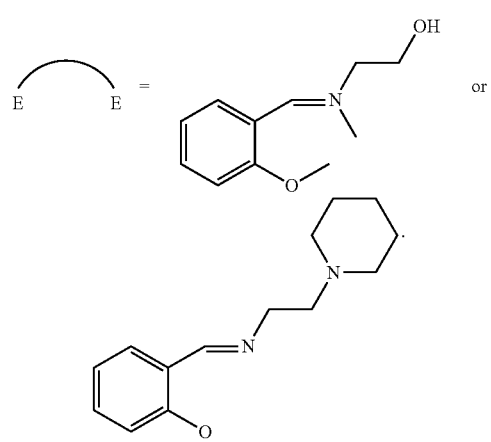

For any of the embodiments, the neutral sigma donor or monovalent anion may be selected from a group consisting of $H_2O$, Cl, Br, F, I, acetate, triflate, perchlorate, nitro, pyridine, ethanol, methanol, tetrahydrofuran, dimethylsulfoxide, carbonate, bicarbonate, sulfate, nitrate and nitrite.

For any of the method embodiments the acid gas scrubbing solvent may include an amine. In one possible embodiment the acid gas scrubbing solvent includes a mixture of (a)

a promoter amine, selected from a group of primary and secondary amines, and (b) a tertiary amine, and/or (c) non-amine chemical compounds.

Such a mixture is described in detail in copending U.S. patent application Ser. No. 13/853,186, filed on Mar. 29, 2013 and entitled "Solvent and Method for Removal of an Acid Gas from a Fluid Stream", the full disclosure of which is incorporated herein by reference. Promoter amines useful in the present method include, but are not limited to, the primary and secondary amines such as 3-N-sulfonylamine (SA), 3-aminopropionitrile (APN), diethyl 2-aminoethanephosphonate (EtP2), N-methyltetrahydrothiophen-3-amine 1,1-dioxide, 2,2'-sulfonyldiethanamine, 3,3'-sulfonyldipropaneamine, 4,4'-sulfonyldibutanenamine, 2-aminoethyl methyl sulfone, 4-aminobutanenitrile, 6-aminohexanenitrile, 3-(methylamino)propanenitrile, diethyl [2-(methylamino)ethyl]phosphonate, diethyl (3-aminopropyl)phosphonate, diethyl (4-aminobutyl)phosphonate, diethyl (5-aminopentyl)phosphonate, diethyl (6-aminohexyl)phosphonate, 2-(tert-butoxy)ethan-1-amine, N-methyl-2-[(2-methyl-2-propanyl)oxy]ethanamine and mixtures thereof.

Tertiary amines and carbonate based salts useful in the present method include but are not limited to methyldiethanolamine (MDEA), triethanolamine (TEA), N,N,-dialkyethanolamine, N,N,N',N'-tetraalky-1,8-naphthalenediamine, N,N,-dialkylbenzylamine, 1,4-dialkylpiperazine, N,N,N',N'-tetraalkyl-1,6-hexanediamine, N,N,N',N'-tetraalkyl-1,5-pentanediamine, N,N,N',N'-tetraalkyl-1,4-butanediamine, N,N,N',N'-tetraalkyl-1,3-propanediamine, N,N,N',N'-tetraalkyl-1,2-ethanediamine, N,N,N',N'-tetrakis(2-hydroxyethyl) ethylenediamine, N,N,N',N',N''-pentaalkyldiethylenetriamine, N,N,N',N',N''-pentaalkyldipropylaminetriamine, N,N,-dialkylcyclohexylamine, N,N,N',N'-tetraalkylbis (aminoethyl)ether, N,N,-dimethyl-2(2-aminoethoxy) ethanol, alkali carbonates where alkyl represents any methyl, ethyl, propyl, butyl isomer, and mixtures thereof. In one possible embodiment, the catalyst compound is provided in the fluid stream with a concentration of between about 0.05 mM and about 50 mM. In another possible embodiment the catalyst compound is provided in the fluid stream with a concentration of between 50.1 mM and 75 mM. In yet another possible embodiment, the catalyst compound is provided in the fluid stream with a concentration of between about 75.1 mM and 100 mM.

Primary and secondary amines useful in the present method include but are not limited to monoethanolamine (MEA), 1-amino-2-propanol (1A2P), 3-amino-1-propanol, 2-amino-1-propanol, 2-amino-1-butanol, 3-amino-2-butanol, 1-amino-2-butanol, 2-(alkylamino)ethanonol (MAE), diglycolamine, morpholine, piperazine (PZ), 1-methylpiperazine (NMP), 2-methylpiperazine, hydroxypiperadine, hydroxymethylpiperazine, 2-piperidineethanol, N-aminoethylpierazine (AEP), aminopropylmorpholine, 4-aminopiperidine, 3-aminopiperidine, 2-amino-piperidine, diethanolamine, 2-amino-2-methyl-1-propanol (AMP), diethanolamine (DEA), diisopropanolamine (DIPA), glycine, alanine, β-alannine, sarcosine, isopropanolamine, benzylamine, ethylene diamine (EDA), 1,3-propanediamine, 1,4-butanediamine, 1,5-pentanediamine, 1,6-hexanediamine.

In any of the embodiments, the catalyst compound must be stable under the relatively high temperature conditions (e.g. between perhaps 70 and 170° C.) found within the stripper 12. The present catalyst compounds meet this requirement.

The following examples further illustrate how to synthesize or manufacture certain representative catalysts used in the method of increasing the overall mass transfer rate of acid gas scrubbing solvents.

Example 1

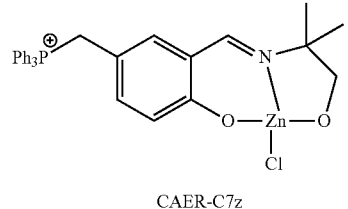

CAER-C7z

Preparation of (H$_2$L7)[Cl]: A 100 mL round bottom flask was charged with 30 mL EtOH and 1-(3-Formyl-4-hydroxybenzyl)-3-triphenylphosphonium chloride (4.334 g, 10.03 mmol). An ethanolic solution of 2-Amino-2-methyl propanol (0.912 g 10.24 mmol) was added drop wise to the solution. The mixture was heated at reflux for two hours. The solvent was removed under vacuum to give yellow solids. The yellow solids were washed with ethanol (3×15 mL) and diethyl ether (3×15 mL) and collected via filtration (4.425 g, 78%).

Preparation of CAER-C7z: A 100-mL round-bottom flask was charged with (H$_2$L7)[Cl] (5.043 g, 10.01 mmol) and EtOH (30 mL) was added to make a colorless slurry. Triethyl amine 3.2 mL (23.023 mmol) was added slowly under vigorous stirring. An ethanolic solution of ZnCl$_2$ (1.632 g, 12.0 mmol, 5 mL) was added drop wise to the mixture. The mixture was heated at reflux for two hours. The solution was cooled to 25° C. and a pale yellow solid precipitated out of solution. The pale yellow solid was collected by filtration and washed with ethanol (3×15 mL) and diethyl ether (3×15 mL) to give the desired product (4.852 g, 85%).

Example 2

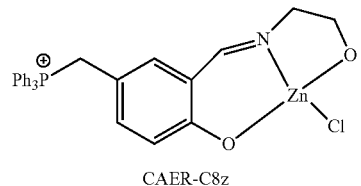

CAER-C8z

Preparation of (H$_2$L8)[Cl]: A 100 mL round bottom flask was charged with EtOH (30 mL) and 1-(3-Formyl-4-hydroxybenzyl)-3-triphenylphosphonium chloride (4.327 g, 10.01 mmol). An ethanolic solution of monoethanolamine (0.9 mL, 15.01 mmol, 5 mL) was added drop wise to the solution and the mixture was heated at reflux for two hours. The solvent was removed under reduced pressure to give a yellow residue. Diethyl ether was added to the reaction vessel and stirred overnight to give a yellow powder which was collected via filtration and washed with diethyl ether (3×30 mL) (4.452 g, 93%).

Preparation of CAER-C8z: A 100-mL round-bottom flask was charged with (H$_2$L8)[Cl] (4.812 g, 10.12 mmol) and EtOH (30 mL) was added to make a clear solution. Triethylamine (3.2 mL, 23.023 mmol) was added slowly while stirring. An ethanolic solution of $ZnCl_2$ (1.687 g, 12.35 mmol, 5 mL)) was added drop wise to the mixture. The mixture was heated at reflux for two hours. The mixture was cooled to 25° C. and a pale yellow solid was collected via filtration and washed with ethanol (3×15 mL) then diethyl ether (3×15 mL) to give the desired product (4.688 g, 86%).

Example 3

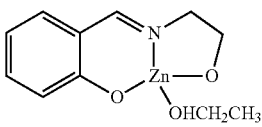

CAER-C9z

Preparation $H_2L9$: A 100-mL round-bottom flask was charged salicylaldehyde (1.95 mL, 16.5 mmol) and EtOH (10 mL) to make a clear solution. Ethanolamine (1 mL, 16.6 mmol) was added dropwise to the above solution with continuous stirring. The solution was stirred at room temperature (25° C.) for one hour and the solvent was removed under vacuum to give the product as a viscous, yellow-orange oil (2.219 g, 81%).

Preparation of CAER-C9z: A 100-mL round-bottom flask was charged with $H_2L9$ (1.656 g, 10.01 mmol) and EtOH (30 mL) to make a clear solution. Triethylamine (3.2 mL, 23.0 mmol) was added while stirring. An ethanolic solution of $ZnCl_2$ (1.687 g, 12.35 mmol, 5 mL) was added dropwise to the mixture. The mixture was heated at reflux for two hours. The mixture was cooled to 25° C. and a pale yellow solid was collected via filtration and washed with ethanol (3×15 mL) then diethyl ether (3×15 mL) to give the desired product (2.199 g, 80%).

Example 4

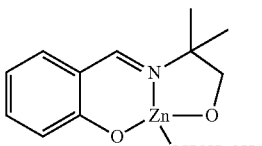

CAER-C10z

Preparation of $H_2L10$: A 100-mL round-bottom flask was charged salicylaldehyde (3 mL, 28.3 mmol) and EtOH (10 mL) to make a clear solution. 2-Amino-2-methyl-1-propanol (2.6775 g, 16.6 mmol) was added to the above solution with continuous stirring. The solution was stirred at room temperature for one hour and the solvent was removed under vacuum to give a yellow residue. The yellow residue was dissolved in dichloromethane (5 mL) and n-pentane was added (20 mL) to produce a yellow powder. The yellow powder was collected via filtration and washed with ether (3×15 mL) to give the desired product (4.767 g, 87%).

Preparation of CAER-C10z: A 100-mL round-bottom flask was charged with $H_2L10$ (1.933, 10.0 mmol) and EtOH (30 mL) to make a clear solution. Triethylamine (3.2 mL, 23 mmol) of was added while stirring. An ethanolic solution of $ZnCl_2$ (1.687 g, 12.35 mmol) was added dropwise to the mixture. The mixture was stirred for 48 hr at room temperature (25° C.). The solvent was reduced under vacuum to 5 mL and acetonitrile was added to the solution to give a pale yellow powder. The pale yellow solid was collected via filtration and washed with acetonitrile (3×15 mL) then diethyl ether (3×15 mL) to give the desired product (2.456 g, 81%).

Example 5

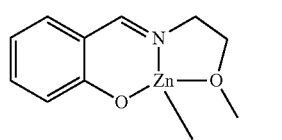

CAER-C11z

Preparation of $H_2L11$: A 100-mL round-bottom flask was charged salicylaldehyde (2.7 mL, 25 mmol) and EtOH (10 mL) to make a clear solution. 2-methoxyethylamine (2 mL, 23 mmol) was added to the solution with continuous stirring. The solution was stirred at room temperature for two hour and the solvent was removed under reduced vacuum to give the desired product as a dark yellow-orange, viscous liquid (3.769 g, 83%).

Preparation of CAER-C11 z: A 100-mL round-bottom flask was charged with $H_2L11$ (1.793, 10.01 mmol) and EtOH (30 mL) to make a clear solution. Triethylamine (3.2 mL, 23 mmol) was added while stirring. An ethanolic solution of $ZnCl_2$ (1.687 g, 12.35 mmol, 5 mL) was added dropwise to the mixture. The mixture was heated at reflux for 3 hours. The solvent was removed under reduced pressure to give a yellow oil. Diethyl ether was added to the oil to give a yellow powder which was collected via filtration. The yellow powder was washed with diethyl ether (3×15 mL) to give the desired product (2.444 g, 85%).

Example 6

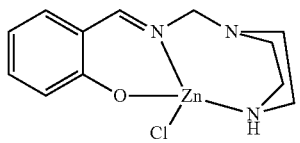

CAER-C12z

Preparation of $H_2L12$: A 100-mL round-bottom flask was charged salicylaldehyde (2.06 mL, 19.5 mmol) and EtOH (10 mL) to make a clear solution. 4-(Aminomethyl)piperidine (2.0256 g, 17.8 mmol) was added to the solution with continuous stirring. The solution was stirred at room temperature for two hours at which point the solvent was removed under reduced pressure to give the desired product as a yellow power (3.521 g, 87%).

Preparation of CAER-C12z: A 100-mL round-bottom flask was charged with $H_2L12$ (2.19, 10.0 mmol) and acetonitrile (30 mL) to make a clear solution. Triethylamine (3.2 mL, 23.023 mmol) was added while stirring. An acetonitrile solution of $ZnCl_2$ (1.776 g, 12.50 mmol) was added dropwise to the mixture. The mixture was stirred at room temperature (25° C.) for 3 hours at which point a yellow powder was generated. The yellow powder was collected via filtration and washed with acetonitrile (3×15 mL) and diethyl ether (3×15 mL) to give the desired product (2.668 g, 83%).

Example 7

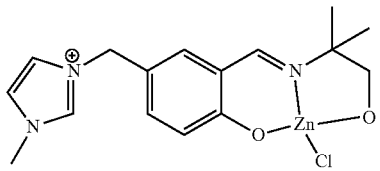

CAER-C13z

Preparation of (H$_2$L13)[Cl]: A 100 mL round bottom flask was charged with EtOH (30 mL) and 5-(1-methylimidazolemethyl)-2-hydroxybenzaldehyde chloride (2.528 g, 10.0 mmol). An ethanolic solution of 2-Amino-2-methyl propanol (0.912 g 10.24 mmol) was added drop wise to the solution. The mixture was heated at reflux for two hours. The solvent was removed under reduced pressure to give a yellow powder which was collected via filtration and washed with ethanol (3×15 mL) and diethyl ether (3×15 mL) to give the desired product (2.872 g, 89%).

Preparation of CAER-C13z: A 100-mL round-bottom flask was charged with (H$_2$L13)[Cl] (3.238 g, 10.01 mmol) and EtOH (30 mL) to make a clear solution. Triethylamine (3.2 mL, 23.023 mmol) was added while stirring. An ethanolic solution of ZnCl$_2$ (1.687 g, 12.35 mmol) was added dropwise to the mixture. The mixture was heated at reflux for two hours at which point a yellow powder was produced which was collected via filtration and washed with ethanol (3×15 mL) then diethyl ether (3×15 mL) to give the desired product (3.123 g, 81%).

Example 8

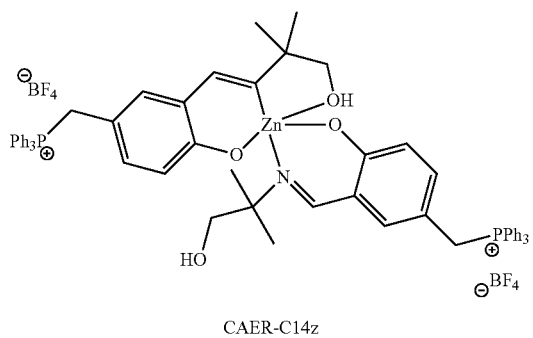

CAER-C14z

Preparation of (H$_2$L7)[BF$_4$]: A 100 mL round bottom flask was charged EtOH (30 mL) and 5-(triphenylphosphinemethyl)-2-hydroxybenzaldehyde tetrafluoroborate (4.842 g, 10.0 mmol) of. An ethanolic solution of 2-Amino-2-methyl propanol (0.912 g 10.2 mmol) was added drop wise to the solution. The mixture was heated at reflux for two hours. The solvent was removed under reduced pressure to give a yellow residue. Diethyl ether was added to the reaction vessel and stirred overnight to give a yellow powder which was collected via filtration and washed with diethyl ether (3×15 mL) to give the desired product (4.956 g, 89%).

Preparation of CAER-C14z: A 100-mL round-bottom flask was charged with (H$_2$L7)[BF$_4$] (1.1108 g, 2.002 mmol) and MeOH (30 mL) to make a colorless slurry. Triethylamine (0.332 m, L 2.30 mmol) was added to the stirred mixture. An ethanolic solution of ZnBF$_4$ (0.2868 g, 1.12 mmol, 5 mL) was added dropwise to the mixture. The mixture was heated at reflux for two hours. The solution mixture was cooled to room temperature (25° C.) to give a yellow powder which was collected via filtration and washed with ethanol (3×15 mL) and diethyl ether (3×15 mL) to give the desired product (1.011 g, 86%).

Example 9

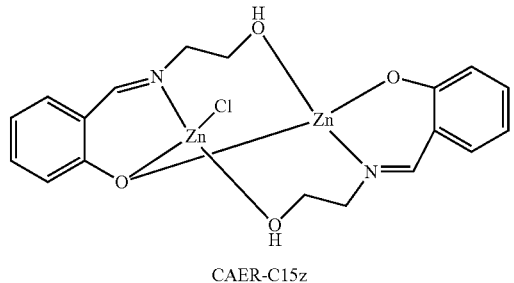

CAER-C15z

Preparation of CAER-C15z: A 100-mL round-bottom flask was charged with H$_2$L9 (1.986 g, 12.02 mmol) and EtOH (15 mL) to make a clear solution. Triethylamine (1.95 mL, 13.8 mmol was added while stirring. An ethanolic solution of ZnCl$_2$ (1.804 g, 13.2 mmol, 5 mL) was added dropwise to the mixture. The mixture was heated at reflux for two hours to give a bright yellow powder which was collected via filtration and washed with ethanol (3×15 mL) then diethyl ether (3×15 mL) to give the desired product (1.8449 g, 62%).

Example 10

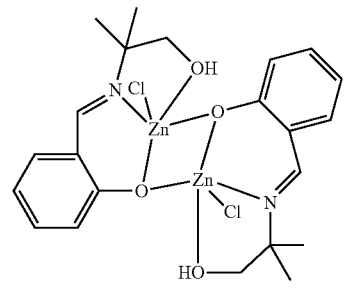

CAER-C16z

Preparation of CAER-C16z: A 100-mL round-bottom flask was charged with H$_2$L10 (5.500 g, 28.5 mmol) and EtOH (20 mL) to make a clear solution. Triethylamine (7.93 mL, 57.0 mmol) was added while stirring. An ethanolic solution of ZnCl$_2$ (4.264 g, 30.8 mmol, 5 mL) was added dropwise to the mixture. The mixture was stirred at room temperature (25° C.) for 48 hr. The solvent was removed under reduced pressure to give a yellow residue and acetonitrile was added to give a yellow powder which was collected via filtration and washed with acetonitrile (3×15 mL) then diethyl ether (3×15 mL) to give the desired product (4.1758 g, 51%).

Example 11

Preparation of CAER-C3p: To a 100-mL round-bottom flask was added [H2LP]C12 (5.002 g, 5.63 mmol), EtOH (40 mL), and triethylamine (1.75 mL, 12.0 mmol) was added to give a clear yellow solution. Zinc chloride (1.363 g, 10.00 mmol) dissolved in EtOH (10 mL) was added, producing a pale yellow slurry. The reaction flask was immersed in a silicon fluid bath at 85° C. and was stirred for 3 h, producing a pale yellow precipitate which was collected via filtration through a medium porosity glass fritted funnel. The pale yellow powder was washed with EtOH then ether (3×20 mL) and air dried to give the desired product (5.679 g, 93%).

The foregoing has been presented for purposes of illustration and description. It is not intended to be exhaustive or to limit the embodiments to the precise form disclosed. Obvious modifications and variations are possible in light of the above teachings. All such modifications and variations are within the scope of the appended claims when interpreted in accordance with the breadth to which they are fairly, legally and equitably entitled.

What is claimed:

1. A compound having a chemical formula:

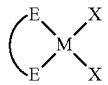

where:
(a) M is any group VII B through XII B element;
(b) x=neutral sigma donor or monovalent anion; and
(c)

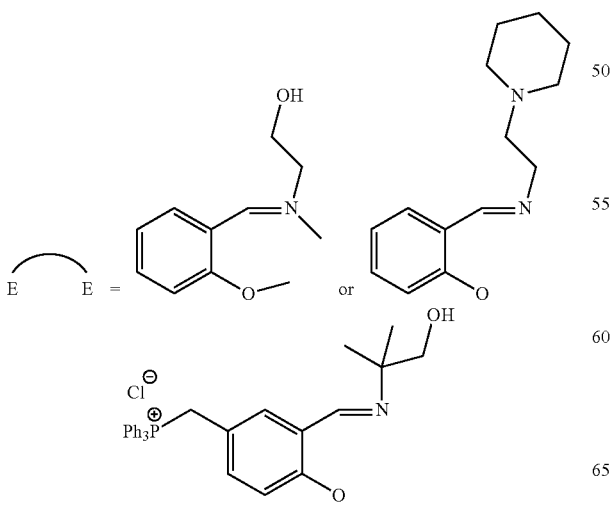

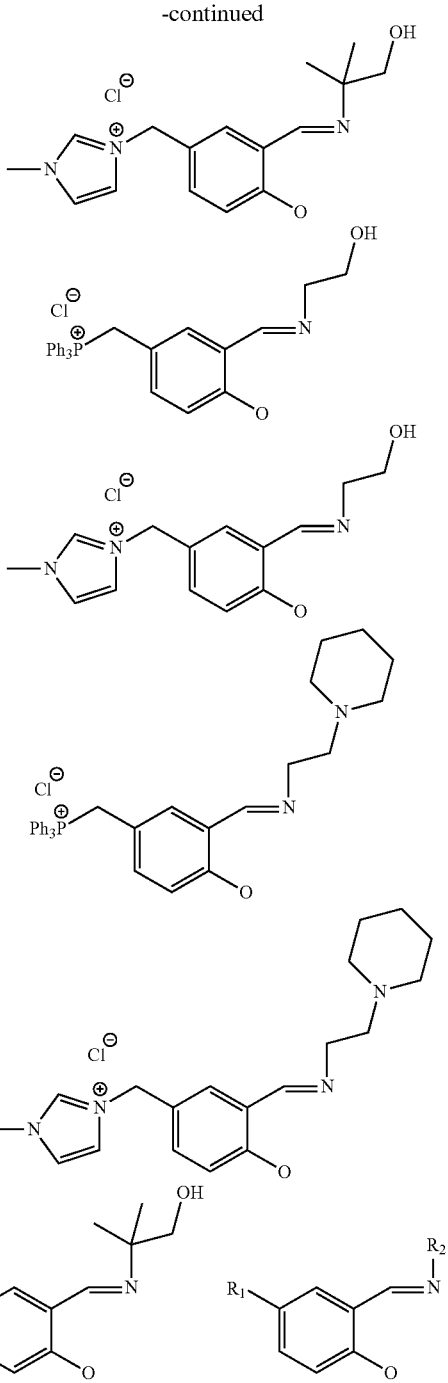

$R_1$=H, any alkyl, RCOOH (R=alkyl ranging from 0-10 carbons); OligoPEG, phosphate, ROH (R=alkyl ranging from 0-5 carbons); OH; $SO_3$; $NO_2$; amine, amide, carbonyl, Cl, Br, I, F, $BH_3$, $[CH_2Q]+[A]-$; and $[CH_2Q]+[A]-=$

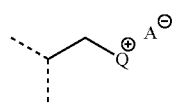

where A=monovalent anion: Cl, Br, I, F, PF$_6$, BF$_4$, acetate, trifluoroacetate, ClO$_4$, NO$_3$, and Q=monovalent cation: P(R)$_3$, R=alkyl, cyclic alkyl, Aryl, O-alkyl, O-Aryl;

N(R)$_3$, R=alkyl, cyclic alkyl, N-heterocyclic ring, imidazole; and

R$_2$=CE; where C=any alkyl, cyclic alkyl, aryl, and E=OH or NH$_2$.

2. A compound consisting of a chemical formula:

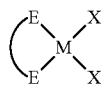

where:
(a) M is any group VII B through XII B element;
(b) x=neutral sigma donor or monovalent anion; and
(c)

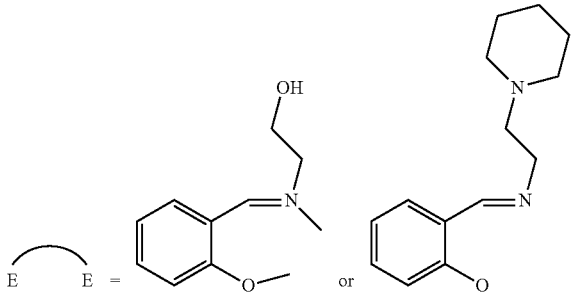

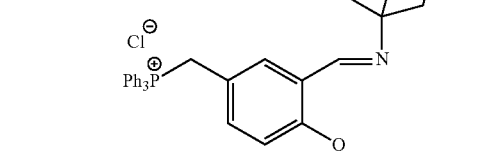

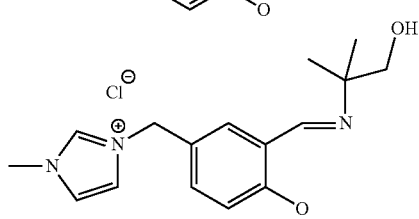

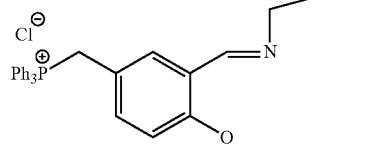

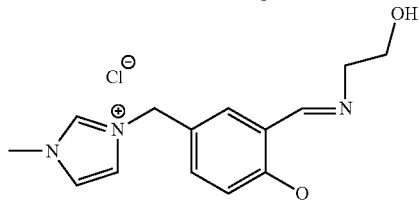

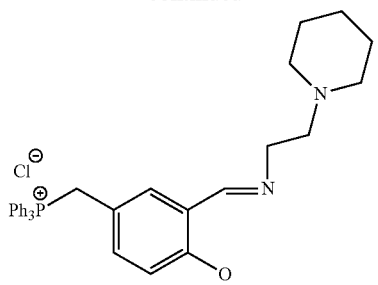

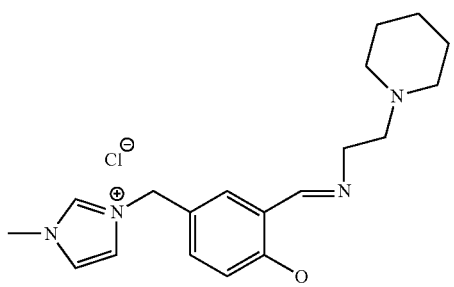

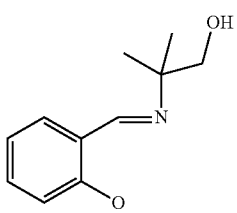 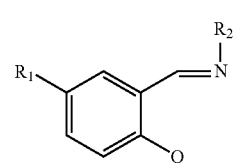

R$_1$=H, any alkyl, RCOOH (R=alkyl ranging from 0-10 carbons); OligoPEG, phosphate, ROH (R=alkyl ranging from 0-5 carbons); OH; SO$_3$; NO$_2$; amine, amide, carbonyl, Cl, Br, I, F, BH$_3$, [CH$_2$Q]+[A]−; and

[CH$_2$Q]+[A]−=

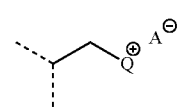

where A=monovalent anion: Cl, Br, I, F, PF$_6$, BF$_4$, acetate, trifluoroacetate, ClO$_4$, NO$_3$, and Q=monovalent cation: P(R)$_3$, R=alkyl, cyclic alkyl, Aryl, O-alkyl, O-Aryl;

N(R)$_3$, R=alkyl, cyclic alkyl, N-heterocyclic ring, imidazole; and

R$_2$=CE; where C=any alkyl, cyclic alkyl, aryl, and E=OH or NH$_2$.

3. A method of increasing overall mass transfer rate of acid gas scrubbing solvents, comprising:
adding a catalyst compound to a fluid stream including an acid gas and an acid gas scrubbing solvent, said catalyst compound having a chemical formula:

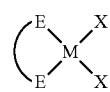

where:
(a) M is any group VII B through XII B element;
(b) x=neutral sigma donor or monovalent anion; and
(c)

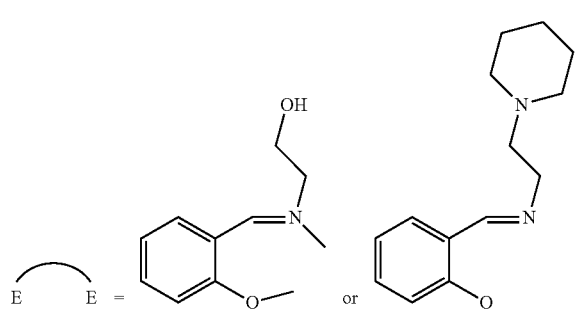

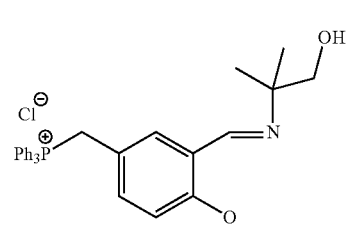

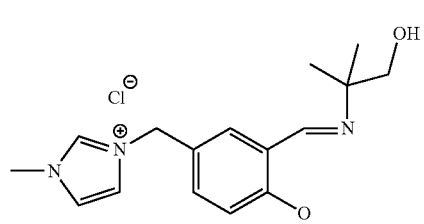

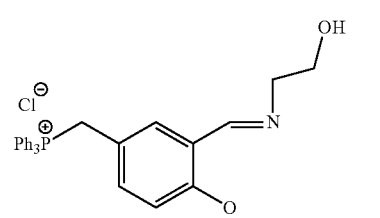

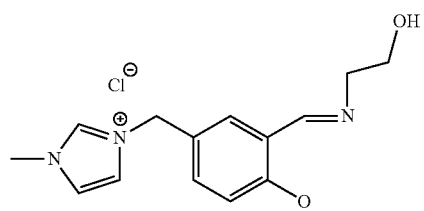

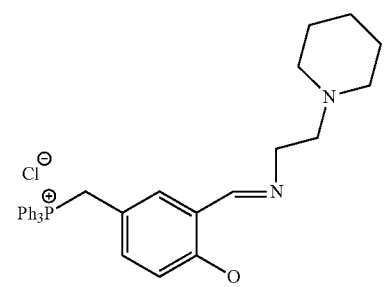

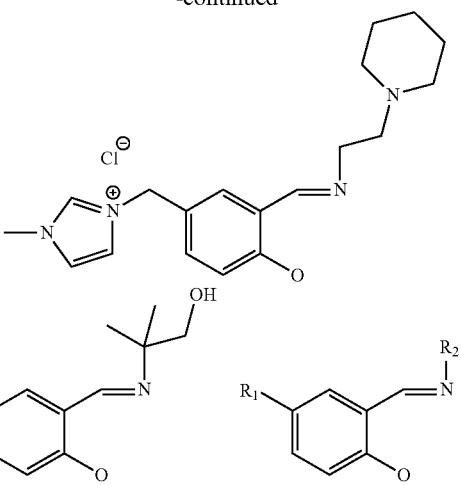

$R_1$=H, any alkyl, RCOOH (R=alkyl ranging from 0-10 carbons); OligoPEG, phosphate, ROH (R=alkyl ranging from 0-5 carbons); OH; $SO_3$; $NO_2$; amine, amide, carbonyl Cl, Br, I, F, $BH_3$, $[CH_2Q]+[A]-$; and $[CH_2Q]+[A]-=$

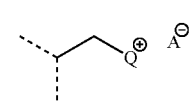

where A=monovalent anion: Cl, Br, I, F, $PF_6$, $BF_4$, acetate, trifluoroacetate, $ClO_4$, $NO_3$, and Q=monovalent cation: $P(R)_3$, R=alkyl, cyclic alkyl, Aryl, O-alkyl, O-aryl $N(R)_3$, R=alkyl, cyclic alkyl, N-heterocyclic ring, imidazole $R_2$=CE; where C=any alkyl, cyclic alkyl, aryl, and E=OH or $NH_2$.

4. The method of claim 3, wherein said neutral sigma donor or monovalent anion is selected from a group consisting of $H_2O$, Cl, Br F, I, acetate, triflate, perchlorate, nitro, pyridine, ethanol, methanol, tetrahydrofuran, dimethylsulfoxide, carbonate, bicarbonate, sulfate, nitrate, nitrite.

5. The method of claim 3, wherein said acid gas scrubbing solvent includes an amine.

6. The method of claim 3, wherein said acid gas scrubbing solvent includes a mixture of a primary amine, secondary amine, or a tertiary amine.

7. The method of claim 3, wherein said acid gas scrubbing solvent includes a material selected from a group consisting of monoethanolamine (MEA), 1-amino-2-propanol (1A2P), 3-amino-1-propanol, 2-amino-1-propanol, 2-amino-1-butanol, 1-amino-2-butanol, 3-amino-2-butanol, 2-(alkylamino) ethanonol (MAE), diglycolamine, morpholine, piperazine (PZ), 1-methylpiperazine (NMP), 2-methylpiperazine, hydroxypiperadine, hydroxyalkylpiperazine, 2-piperidineethanol, N-aminoethylpierazine (AEP), aminopropylmorpholine, 4-aminopiperidine, 3-aminopiperidine, 2-amino-piperidine, diethanolamine, 2-amino-2-methyl-1-propanol (AMP), diethanolamine (DEA), diisopropanolamine (DIPA), glycine, alanine, R-alannine, sarcosine, isopropanolamine, benzylamine, methyldiethanolamine (MDEA), triethanolamine (TEA), alkali carbonate, N,N,-dialkylethanolamine, N,N,N',N'-tetraalky-1,8-naphthalenediamine, N,N,-dialkylbenzylamine, 1,4-dialkylpiperazine, N,N,N',N'-tetraalkyl-1,6-hexanediamine, N,N,N',N'-tetraalkyl-1,5-pentanediamine, N,N,N',N'-tetraalkyl-1,4-butanediamine, N,N,N',N'-tetraalkyl-1,3-propanediamine, N,N,N',N'-tetraalkyl-1,2-ethanediamine, N,N,N',N'-tetrakis(2-hydroxyethyl)ethylenediamine, N,N,N',N',N''-pentaalkyldiethylenetriamine, N,N,N',N',N''-pentaalkyldipropylaminetnamine, N,N,-dialkylcyclohexylamine, N,N,N',N'-tetraalkylbis(aminoethyl)ether, N,N,-dimethyl-2(2-aminoethoxy)ethanol, where alkyl represents any methyl, ethyl, propyl, butyl isomer, and mixtures thereof.

8. The method of claim 3, wherein said catalyst compound is provided at a concentration of between about 0.05 mM and about 100 mM.

\* \* \* \* \*